(12) United States Patent
Lange (10) Patent No.: US 6,788,404 B2
(45) Date of Patent: Sep. 7, 2004

(54) INSPECTION SYSTEM WITH MULTIPLE ILLUMINATION SOURCES

(75) Inventor: Steven R. Lange, Alamo, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/268,340

(22) Filed: Oct. 9, 2002

(65) Prior Publication Data

US 2004/0012774 A1 Jan. 22, 2004

Related U.S. Application Data

(60) Provisional application No. 60/396,709, filed on Jul. 17, 2002.

(51) Int. Cl.[7] .............................................. G01N 21/00
(52) U.S. Cl. .................................. 356/237.2; 356/237.5
(58) Field of Search .......................... 356/237.1–237.5, 356/369, 394, 630–632; 256/630–631

(56) References Cited

U.S. PATENT DOCUMENTS

| | | | | |
|---|---|---|---|---|
| 5,900,939 A | * | 5/1999 | Aspnes et al. | 356/369 |
| 6,288,780 B1 | * | 9/2001 | Fairley et al. | 356/237.1 |
| 6,583,876 B2 | * | 6/2003 | Opsal et al. | 356/369 |

* cited by examiner

Primary Examiner—Hoa Q. Pham
(74) Attorney, Agent, or Firm—Beyer Weaver & Thomas LLP (57) ABSTRACT

The present invention pertains to techniques for increasing the available illumination light, increasing the resolution, and optimizing the spectrum of optical inspection systems. These techniques involve combining the light beams from two or more separate illumination sources. In one embodiment, this performed by utilizing two separate illumination sources wherein one of the illumination sources compensates the other illumination source in the wavelength range where illumination light intensity is low. Specifically, this can be performed by utilizing a broadband illumination source and a narrowband illumination source combined with dichroic beamsplitters.

22 Claims, 6 Drawing Sheets

INSPECTION SYSTEM WITH MULTIPLE ILLUMINATION SOURCES

CROSS REFERENCE TO RELATED APPLICATIONS

This application claims priority of U.S. Provisional Patent Application No. 60/396,709, filed Jul. 17, 2002, which application is incorporated herein by reference in its entirety for all purposes.

FIELD OF THE INVENTION

The present invention relates generally to optical inspection systems, and more specifically to illumination techniques for optical inspection systems.

BACKGROUND OF THE INVENTION

Optical inspection systems are commonly used in semiconductor manufacturing processes for quality control purposes. Specifically, optical inspection systems are used to detect and locate manufacturing defects. Optical inspection systems use an illumination source to illuminate the specimen being inspected. Various characteristics of the illumination source affect the resolution of the inspection system and the types of defects that can be detected. For instance, the intensity of the light produced from the light source affects the speed of the optical examination, and the wavelength of the light affects the types of defects that can be detected. Typically, more defect types and smaller defects can be detected when inspection is performed using shorter wavelength light because resolution is greater. Naturally, many inspection systems are designed to have high intensity and short effective wavelength illumination. Short effective wavelength illumination refers to an illumination source that produces light over a range of wavelengths such that the average wavelength is relatively short.

One type of illumination source used by optical inspection systems is an arc lamp. Arc lamps are broadband illumination sources in that they produce light in a broad range of wavelengths. A common arc lamp, for example, a mercury (Hg) arc lamp can produce light in the range of 200–600 nanometers (nm). Broadband illumination sources are advantageous since material contrast and scattering is affected by wavelength, and these mechanisms are important in maximizing the signal-to-noise ratio for detecting a variety of features and/or defects. They are also advantageous because the diversity of wavelengths in the illumination mitigates thin-film interference effects due to process variation produced thickness variations in transparent films (this interference is a noise source because it is generally not well-controlled on wafers). However, the intensity value within the range of wavelengths can vary among various sub-ranges of wavelengths because the intensity of light produced by arc lamps vary greatly from wavelength to wavelength. For example, Hg arc lamps produce light having spikes of high intensity at certain wavelengths while the intensity between such spikes is generally much lower. Also, these high intensity spikes tend to be located near the mid to longer wavelength end of the operational range of Hg arc lamps. As a result, optical inspection systems utilizing Hg arc lamps tend to have lower intensity in the shorter wavelength ranges, for example, in the wavelength range below approximately 300 nm. Practically, this means that the amount and quantity of information available from optical inspection systems can be limited by the characteristics of the illumination source. In light of the foregoing, optical inspection systems with increased resolution capabilities would be desirable.

BRIEF SUMMARY OF THE INVENTION

The present invention pertains to techniques for increasing the intensity and resolution of optical inspection systems. These techniques involve combining the light beams from two separate illumination sources within a single optical inspection system. One implementation of the invention involves the utilization of a broadband illumination source and a narrowband illumination source. In such an implementation, one of the illumination sources can compensate the other illumination source in the wavelength range where illumination light intensity is low.

The technique of combining illumination light sources has many advantages aside from increasing the resolution. For instance, the speed of inspection devices can be increased because the overall available optical power is increased. Also, the equivalent spectral range where the inspection system operates can be relocated. In other words, the effective wavelength of the illumination source can be shortened in order to increase the resolution of the inspection system. Additionally, the operational spectrum of wavelengths used for inspection can be broadened. Broadband illumination sources are advantageous in that interference effects are minimized, maximum material contrast is provided due to either thin-film interference or scattering, and the amount of "color" noise in the inspection system is reduced. Furthermore, the combination of a short wavelength narrowband source with a conventional broadband source more closely approximates an ideal illumination source, which is both broadband and has high intensities in the shorter wavelengths.

These and other features and advantages of the present invention will be presented in more detail in the following specification of the invention and the accompanying figures, which illustrate by way of example the principles of the invention.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known operations have not been described in detail so not to unnecessarily obscure the present invention.

The present invention pertains to techniques for increasing the light intensity and resolution of optical inspection systems. These techniques involve combining the light beams from two separate illumination sources by dichroic beamsplitters. For instance, a broadband illumination source and a narrowband illumination source can be combined to produce a combined light beam having parameters that produce better inspection results.

Figure 1:
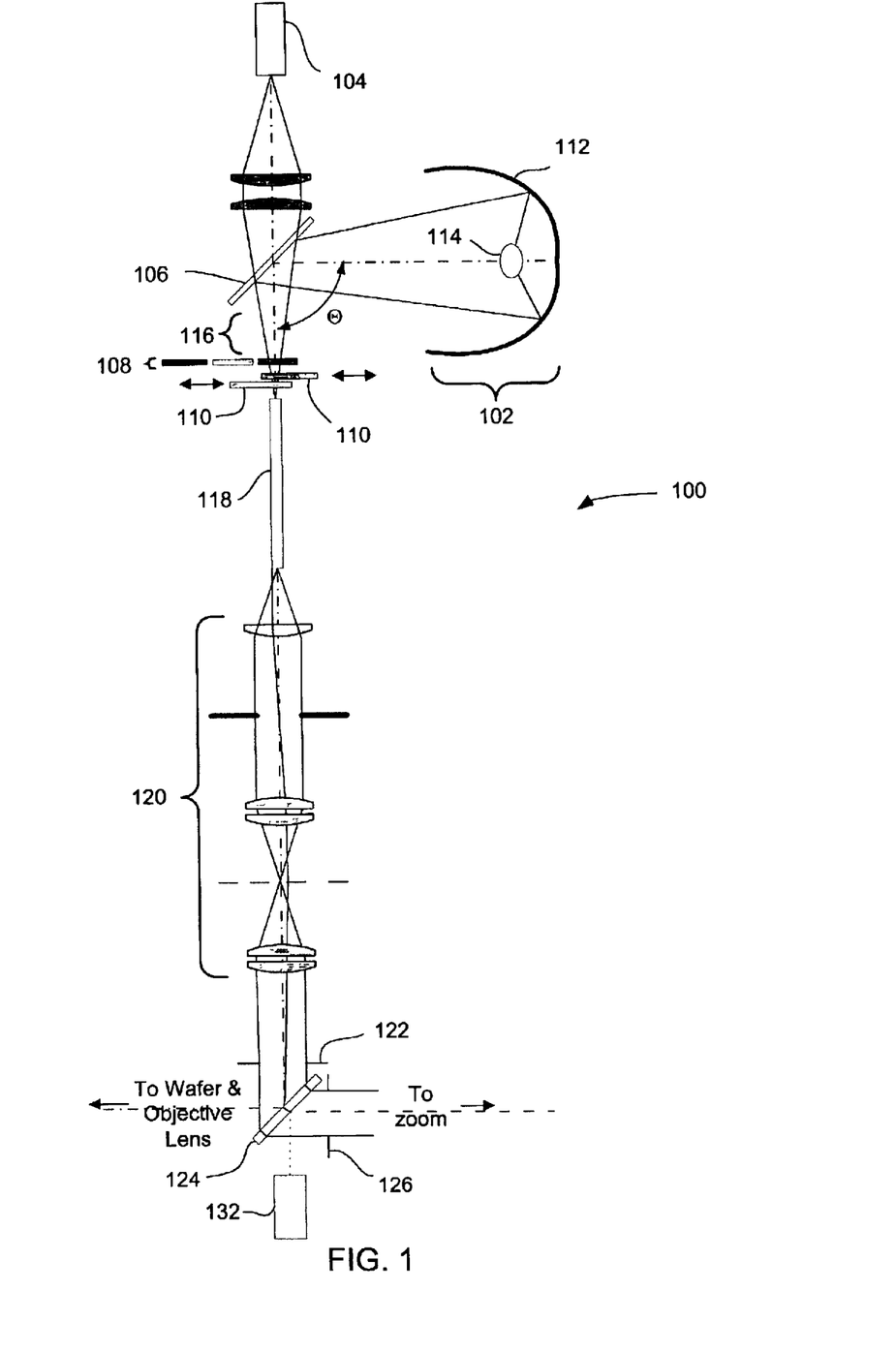
FIG. 1 illustrates a partial diagrammatic view of one embodiment of an optical inspection system of the present invention in which a broadband and a narrowband illumination source are utilized.

FIG. 1 illustrates a partial diagrammatic view of one embodiment of an optical inspection system 100 of the present invention in which a broadband 102 and a narrowband 104 illumination source are utilized. Illumination sources 102 and 104 direct respective light beams into optical inspection system 100 such that the light beams pass through various lens and filters until the semiconductor wafer specimen (not shown) is ultimately illuminated for inspection. The description of FIG. 1 will now concentrate on the configuration used to combine the light beams from illumination sources 102 and 104. In this embodiment, illumination source 102 is an arc lamp and illumination source 104 is a laser light source and they direct light beams that become coincident with each other at a dichroic beamsplitter 106. Dichroic beamsplitter 106 is designed to transmit light at one wavelength incident upon one surface and reflect light at another wavelength that is incident upon the other surface. In FIG. 1, the light beam from arc lamp 102 reflects off dichroic beamsplitter 106 so that it is redirected through color filters 108 and neutral density filters 110. At the same time, the light beam from laser illumination source 104 is transmitted through dichroic beamsplitter 106 so that it also reaches color filters 108 and neutral density filters 110. After transmitting and reflecting off of dichroic beamsplitter 106 respectively, the light beams from narrowband 104 and broadband 102 illumination sources join into a combined light beam 116 that will be channeled to illuminate the specimen. As will be described in more detail below, the single light beam has the combined beneficial characteristics from each of illumination sources 102 and 104.

As shown in FIG. 1, the light beams from illumination sources 102 and 104 intersect each other at approximately a 90-degree angle. Also, light from illumination source 102 reflects off of dichroic beamsplitter 106 at a reflection angle θ, which is also approximately 90 degrees. The relative angle between illumination sources 102 and 104 can vary depending upon specific design parameters of the coatings for the dichroic beamsplitter. For the various relative angles at which illumination sources 102 and 104 can be positioned, dichroic beamsplitter 106 should be angled to appropriately direct light rays into inspection system 100.

In order for the light beams from each of the illumination sources 102 and 104 to properly join into a single beam to illuminate the specimen, the two beams should have approximately the same LaGrange Invariant at the point where they combine. Specifically, the two light beams should have the same LaGrange Invariant at dichroic beamsplitter 106. Having the same LaGrange Invariant means that the light from the two illumination sources will have approximately the same distribution of light. In other words, when two light sources are combined, the size and angular extent of the respective light beam will match. The angular extent refers to the range of angles across which the light rays project. For example, at dichroic beamsplitter 106, the light from illumination source 102 and 104 should match each other in size and angular extent.

In FIG. 1, the components of arc lamp illumination source 102 that are shown are a reflective ellipse 112 and an arc lamp 114. Reflective ellipse 112 directs the light produced from arc lamp 114 towards dichroic beamsplitter 106. Laser illumination source 104 emits radiation continuously over the integration period of the inspection detectors, which is approximately 1 millisecond in length. Therefore, a continuous-wave laser, a mode-locked laser (approximately 80 mega Hertz), or a Q-switched laser having frequencies greater than 50 kilo Hertz) can be used for illumination source 104. However, pulsed excimer lasers can also be used. For example, 248 nm KrF lasers, 308 nm XeCl lasers, and 351 nm XeF lasers can also be used.

Note that laser illumination source 104 is actually a laser combined with a spatial coherence-busting device. The spatial coherence-busting device is for example a rotating ground piece of glass or a phase plate through which the laser passes. As is known in the art, spatial coherence-busting devices are used to integrate laser devices with optical inspection systems.

A light level sensor 132 is located proximate to dichroic beamsplitter 124. Light level sensor 132 is usually positioned downstream of variable neutral density filters 110 and color filters 108. Light level sensor 132 detects light levels at dichroic beamsplitter 106 to monitor the amount of light coming from each of the illumination sources 102 and 104. Light level sensor 132 is capable of detecting the intensity of each of broadband light source 102 and narrowband light source 104. Light level sensor 132 is used to set the respective light power of broadband and narrowband illumination sources 102 and 104 quickly without involving reflected light from the wafer or a camera. As is commonly understood, it is time consuming to use cameras since they typically have thousands of pixels that must be combined somehow (i.e., averaging the pixels) to get a single light level reading. In one embodiment, light level sensor 132 has two photodiodes and a dichroic beamsplitter.

Figure 2:
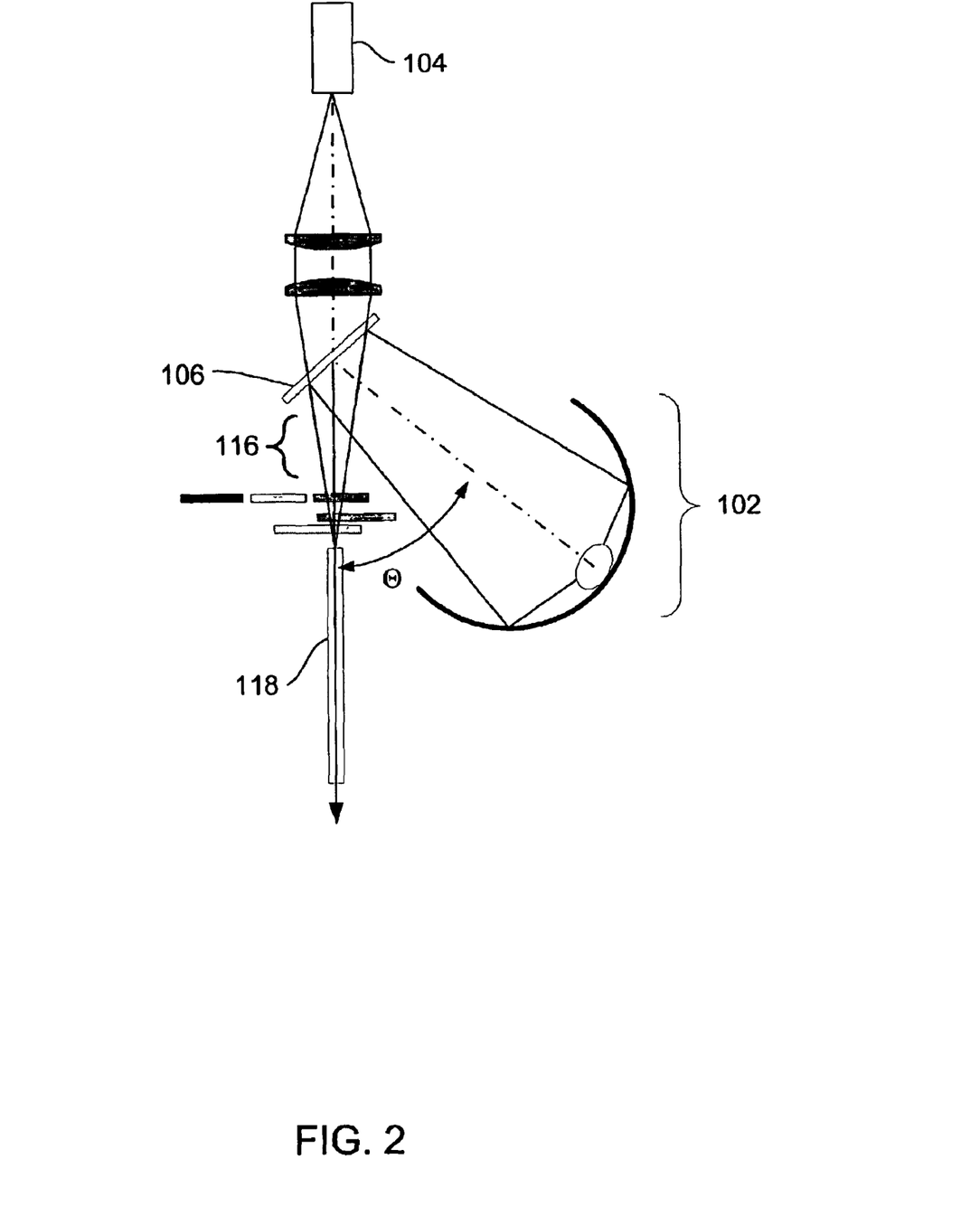
FIG. 2 illustrates an alternative embodiment of the present invention wherein the broadband illumination source is placed at a lower incident angle θ with respect to a dichroic beamsplitter.

FIG. 2 illustrates an alternative embodiment of the present invention wherein illumination sources 102 and 104 are positioned such that illumination source 102 is placed at a lower reflection angle θ with respect to dichroic beamsplitter 102. The lower reflection angle allows the coatings on dichroic beamsplitter 106 to more efficiently reflect light from illumination source 102 and transmit light from illumination source 104 into inspection system 100. Optical lens elements are commonly coated with materials to improve the optical spectral transmission and reflection of the optical system. For instance, optical lens elements are commonly coated with anti-reflective coatings to improve transmission. Optimal reflection angles are a function of the wavelength and wavelength ranges of each illumination source. Typically, the minimum angle of reflection is preferred. However, the angle of reflection is usually limited by structural considerations. For example, the various components must be arranged so that they do not obstruct the light beam within the inspection system.

In alternative embodiments of the present invention, the broadband and narrowband illumination sources 102 and 104 can be configured to either reflect or transmit its respective light beams through dichroic beamsplitter 106. Therefore with respect to FIG. 1, the positions of broad and narrowband illumination sources 102 and 104 can be switched such that broadband illumination source transmits a light beam through dichroic beamsplitter 106 and narrowband illumination source 104 reflects light off of beamsplitter 106.

The structure of inspection system 100 below dichroic beamsplitter 106 will now be described. After light from illumination sources 102 and 104 are combined into combined light beam 116, spectral filters (also referred to as color filters) are used to shape the spectra of combined light beam 116 for the purpose of minimizing color interference and selecting the effective wavelength of the system to maximize the signal-to-noise ratio. It should be noted, however, that spectral filters diminish light transmission.

Neutral-density filters 110 cut down the total amount of light across a spectrum regardless of wavelength. Specifically, neutral-density filters 110 adjust the combined light beam produced by illumination sources 102 and 104.

The ratio of light within combined light beam 116 that comes from each of narrowband illumination source 104 and broadband illumination source 102 can be adjusted in several manners. One manner involves using an intensity adjustable laser. Another involves positioning a polarizer between illumination source 104 and dichroic beamsplitter 106 to control the light from the laser. Yet another manner involves placing a neutral density filter in front of one or both of illumination sources 102 and 104. One reason to adjust the light of illumination source 102 relative to illumination source 104 is to control thin-film interference, which is color noise due to process variations during wafer fabrication processes. Another reason is to maximize the signal to noise ratio, which can be affected by color noise, scattering or diffraction efficiency of the defect compared to its surrounding structures, which are wavelength dependent.

After passing through filters 108 and 110, the light beam passes through light pipe 118. Light pipe 118 randomizes the spatial distribution of the light rays that pass through it. The passing light beam exits light pipe 118 with a more spatially uniform distribution. This spatial distribution allows inspection system 100 to produce more consistent analysis results.

After exiting light pipe 118, the light beam passes through a section of optical lenses 120 designed to match the light beam's properties to the properties of the objective lens for the system. This set of optical lenses, referred to as the illumination lens section 120, directs light through an illumination pupil 122. Illumination pupil 122 can be adjusted in shape to allow specific sections of the illuminating light beam to pass so that the specimen can be illuminated in a variety of manners. After passing through illumination pupil 122, a beamsplitter 124 redirects the illuminating light through an objective lens section (not shown). Light returning from the specimen (not shown) travels back through the objective lens and then through beamsplitter 124, to a collection pupil 126, and a zoom lens (not shown) until it reaches light detectors for analysis. Collection pupil 126 is also variable in shape so that various types of inspection can be performed. The aperture of illumination pupil 122 and collection pupil 126 are configured together for various illumination techniques. Various illumination techniques include those of darkfield, brightfield, high-sigma, as well as other illumination/collection modes that maximize signals of defects with respect to wafer background noise on inspected wafers.

Figure 3:
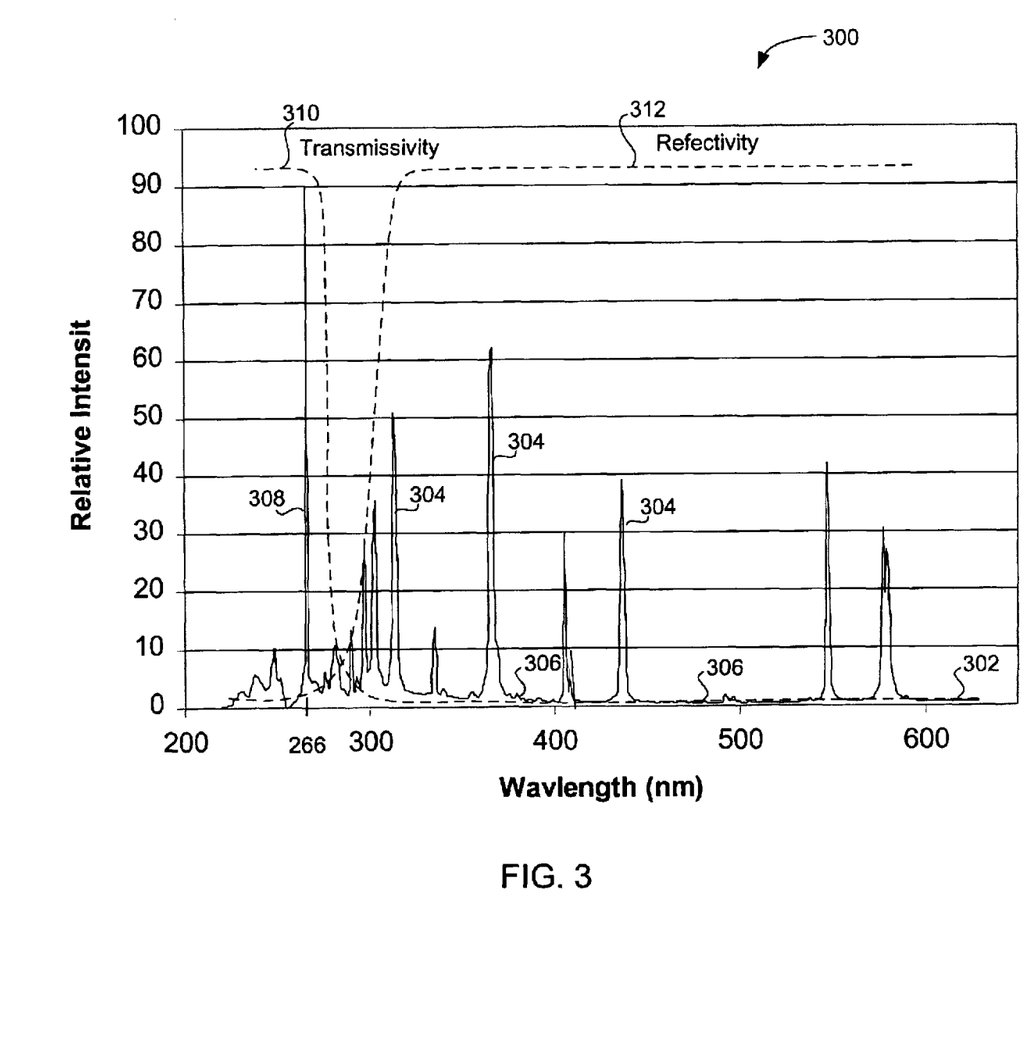
FIG. 3 shows a graph of light intensities for the illumination sources of FIG. 1 as a function of wavelength.

Inspection systems utilizing techniques of the present invention typically operate in short wavelength ranges of the electromagnetic spectrum. Such wavelength ranges include the ultraviolet and deep ultraviolet range, which ranges between approximately 190–370 nanometers. However, the present invention can be utilized in inspection systems operating in various wavelength ranges. FIG. 3 shows a graph 300 of light intensities for illumination sources 102 and 104 of FIG. 1 as a function of wavelength. Curve 302 contains numerous high intensity spikes 304 interspersed throughout low intensity stretches 306. All of spikes 304 are produced by broadband illumination source 102 except for spike 308, which is at approximately 266 nm. In some embodiments, a frequency doubled 532 nm doubled Yag laser produces the light at 266 nm. Spike 308 represents an intense and narrowband beam of light produced by narrowband illumination source 104. As seen in FIG. 3, most of the intensity of broadband illumination source 102 is at wavelengths above approximately 300 nm. Table 1 lists the normalized intensities of Hg broadband illumination source 102. As shown in Table 1, approximately 44.5% of the total intensity of broadband illumination source 102 is located at 365.6 nm and approximately 21.2% of the total intensity is located at 313.3 nm. Only a small percentage of the total light intensity is located below approximately 300 nm. Without narrowband illumination source 104, resolution of inspection system 100 is higher at wavelengths above approximately 300 nm. Narrowband illumination source 102, however, greatly increases the light intensity of inspection system 100 at lower wavelengths (i.e., below 300 nm) since it is located at approximately 266 nm. Additionally, illumination source 102 lowers the effective wavelength of inspection system 100.

TABLE 1

Normalized Intensity of Hg Arc Lamp

| Wavelength (nm) | Normalized Intensity |
|---|---|
| 248.7 | 0.034 |
| 265.8 | 0.033 |
| 281.0 | 0.036 |
| 290.5 | 0.026 |
| 297.1 | 0.066 |
| 302.9 | 0.094 |
| 313.3 | 0.212 |
| 335.2 | 0.053 |
| 365.6 | 0.445 |

In alternative embodiments, illumination source 104 can be adjusted or replaced so that spike 308 is produced at different wavelengths. The position of spike 308 can be adjusted relative to specific inspection requirements. For instance, spike 308 can be adjusted to increase system resolution for specific features, to broaden the spectrum of inspection wavelengths, or to lower the effective inspection wavelength.

The low wavelength light from narrowband illumination source 104 tends to lower the effective wavelength of the inspection system. This tends to increase the resolution of the inspection system since the resolution is proportional to the effective wavelength of the illumination source. Specifically, resolution=$\lambda$/(numerical aperture of system).

Placing narrowband illumination source 104 at the low end of the operational spectrum also tends to broaden the operational spectrum. This tends to reduce the effective coherence length of the system and reduce interference effects caused by thin transparent films on the wafer. Broadening of the spectrum can be accomplished in various manners. In one embodiment, a second narrowband illumination source can be placed at the long wavelength end of the operational spectrum. It is understood that optical limitations will limit the ability to broaden the inspection spectrum. For example, color-based aberrations in the optical lenses and the bandwidth of lens coatings for high transmission (antireflection) and reflection (mirror) create such limitations.

In situations where the narrowband illumination source is sufficiently intense, the broadband illumination source can be turned off or completely blocked out such that illumination is solely from the narrowband illumination source. This can be advantageous to further decrease the effective wavelength of the system and to increase resolution. This is possible if process variations do not make color interference problems worse. On the other hand, the broadband illumination source can be used without illumination from the narrowband illumination source for inspecting wafers that have strong color noise.

Dashed lines 310 and 312 represent the transmissivity and reflectivity indexes, respectively, of coatings formed on the surfaces of dichroic beamsplitter 106. These coatings are designed so that dichroic beamsplitter 106 acts to transmit light from illumination source 104 and reflect light from illumination source 102. Dashed line 310 shows that a transmissive coating formed on dichroic beamsplitter 106 is designed to transmit only light at the lower operational range of Hg illumination source 102 such that light at spike 308 passes through dichroic beamsplitter 106. On the other hand, dashed line 312 shows that a reflective coating forces is designed to allow light at wavelengths at greater than approximately 300 nm to reflect off of dichoric beamsplitter 106. In other embodiments of the inspection system, these coatings are modified to properly reflect and transmit light from the different illumination sources.

Figure 4:
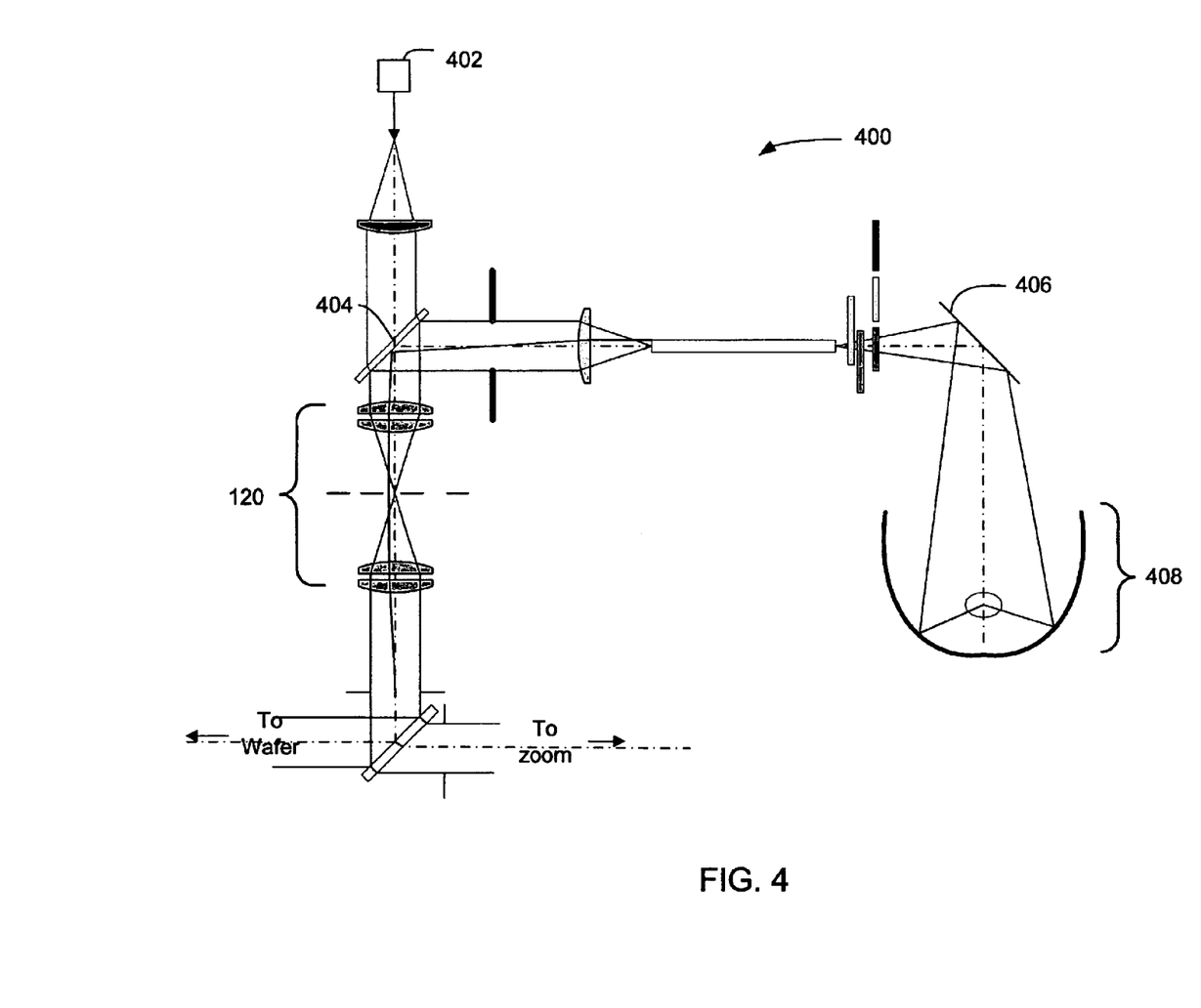
FIG. 4 illustrates an alternative embodiment of an optical inspection system of the present invention.

FIG. 4 illustrates an alternative embodiment of an optical inspection system 400 of the present invention. Optical inspection system 400 is very similar to the system of FIG. 1 except that system 400 is configured so that a narrowband illumination source 402 produces a light beam that joins a broadband light beam in a section before illumination lens section 120. In system 400, dichroic beamsplitter 404 performs the same function, however, it is placed before illumination lens section 120. A cold mirror 406 is used to direct the light beam from broadband illumination source 408 into inspection system 400. As before, the LaGrange Invariant of the light beams from sources 402 and 408 must match in order to properly combine at dichroic beamsplitter 404. It should be noted that the inspection system of the present invention could be configured to join light beams from each light source at various positions within the system.

Figure 5:
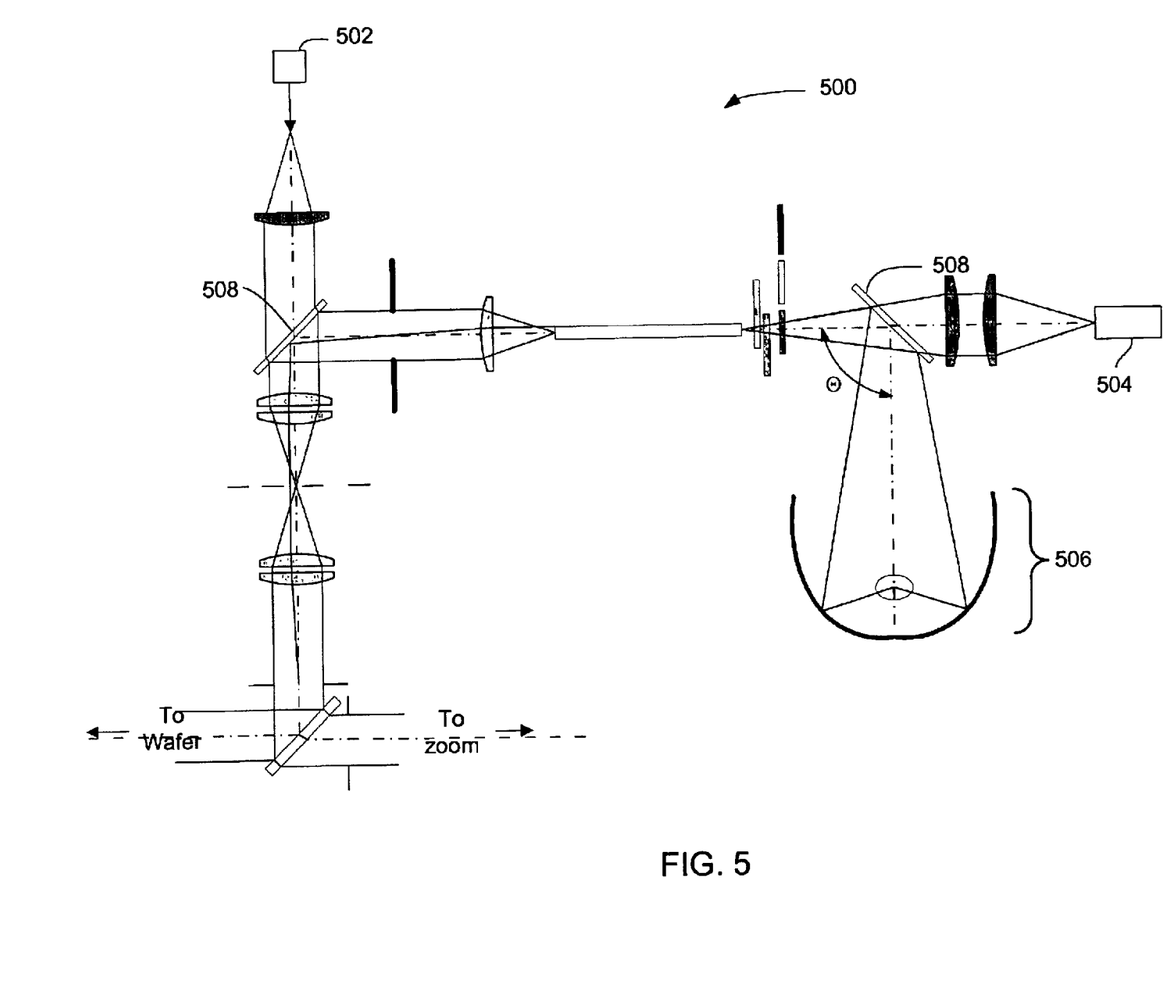
FIG. 5 illustrates another embodiment of an optical inspection system where two narrowband illumination sources supplement a broadband illumination source.

FIG. 5 illustrates another embodiment of an optical inspection system 500 where two narrowband illumination sources 502 and 504 supplement a broadband illumination source 506. In this configuration, narrowband illumination sources are positioned at each of the positions described in FIGS. 1 and 4. A dichroic beamsplitter 508 is used at each location. The additional narrowband illumination source is used to further shape the inspection spectrum. By selecting appropriate laser wavelengths and/or filtering out undesired wavelengths from the broadband source, an illumination spectrum can be created that is well suited to the characteristics of the wafer being inspected. For example, the resolution of the inspection system can be tuned for specific materials, topographic features, etc. Also, color interference noise can be further reduced. Each narrowband illumination source 502 and 504 injects a high intensity light beam to increase the inspection system's resolution. In one embodiment, both of the narrowband illumination sources 502 and 504 produce light beams at the short end of the wavelength range of the broadband illumination source. For instance, one of the narrowband illumination sources produces light at 266 nm and the other narrowband illumination source produces light at 257 nm. In another embodiment, narrowband light beams at 266 nm and 355 nm are used.

Figure 6:
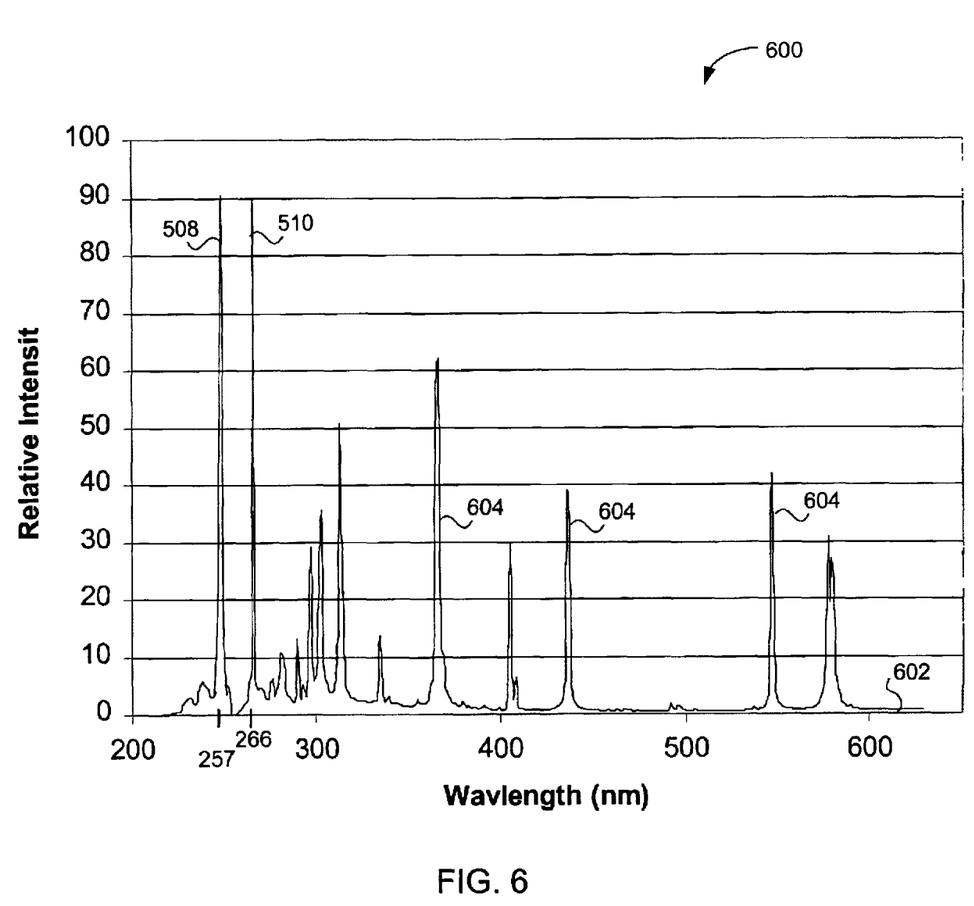
FIG. 6 shows a graph of light intensities for the illumination sources of FIG. 5 as a function of wavelength, according to one embodiment of the present invention.

FIG. 6 shows a graph 600 of light intensities for illumination sources 502, 504 and 506 of FIG. 5 as a function of wavelength, according to one embodiment of the present invention. Curve 602 contains numerous intensity spikes 604 that are predominantly representative of light produced by broadband illumination source 506. Spikes 508 and 510, however, represent the intensity of light produced by each of narrowband illumination sources 502 and 504. In yet other embodiments of the system configuration of FIG. 5, illumination sources 502 and 504 can be set to produce narrowbands of light at the edges of the operational spectrum of broadband illumination source 506 so to broaden the illumination spectrum.

In other embodiments of the present invention, a combination of light sources can include two broadband sources. In other embodiments, two narrowband illumination sources can be combined. In either embodiment, the narrowband sources can be single frequency lasers or multi-frequency lasers (such as an Argon-ion laser).

While this invention has been described in terms of several preferred embodiments, there are alteration, permutations, and equivalents, which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

I claim:

1. An optical inspection system for semiconductor inspection comprising:
   a first illumination source that directs a first light beam into the optical inspection system in order to illuminate a semiconductor specimen; and
   a second illumination source that directs a second light beam into the optical inspection system in order to further illuminate the semiconductor specimen,
   the first and second light sources producing light within the wavelength range of 100–700 nanometers,
   the first and the second light beams being coincident with each other at a dichroic beamsplitter such that the first and second light beams have approximately the same LaGrange Invariants at the dichroic beamsplitter, whereby the first and second light beams are used together for inspection purposes.

2. An optical inspection system for semiconductor inspection as recited in claim 1 wherein the first and second illumination sources are broadband illumination, sources.

3. An optical inspection system for semiconductor inspection as recited in claim 1 wherein the fist and second illumination sources are narrowband illumination sources.

4. An optical inspection system for semiconductor inspection comprising:
   a broadband illumination source that directs a broadband light beam into the optical inspection system in order to illuminate a semiconductor specimen; and
   a narrow band illumination source that directs a narrowband light beam into the optical inspection system in order to further illuminate the semiconductor specimen, wherein the broadband and the narrowband light beams are coincident with each other at a dichroic beamsplitter such that the broadband and the narrowband light beams have approximately the same LaGrange Invariants at the dichroic beamsplitter, whereby the broadband and the narrowband light beams are used together for inspection purposes.

5. An optical inspection system as recited in claim 4 wherein the broadband illumination source reflects off of the dichroic beamsplitter and the narrowband illumination source transmits through the dichroic beamsplitter.

6. An optical inspection system as recited in claim 4 wherein the narrowband illumination source reflects off of the dichroic beamsplitter and the broadband illumination source transmits through the dichroic beamsplitter.

7. An optical inspection system as recited in claim 4 wherein one of the narrowband the broadband illumination sources reflects off of the dichroic beamsplitter at a reflection angle of approximately 90 degrees or less.

8. An optical inspection system as recited in claim 4 wherein the broadband light beam spans a first range of wavelengths wherein the intensity of light within the first range is lower at the lower end of the first range, and wherein the narrowband light beam spans a second range of wavelengths wherein the intensity of light within the second range is approximately constant, the second range of wavelengths being positioned within the lower end of the first range.

9. An optical inspection system as recited in claim 4 wherein the broadband light beam spans a first range of wavelengths, and wherein the narrowband light beam spans a second range of wavelengths, the second range of wavelengths being positioned within the shorter end of the first range thereby lowering the effective inspection wavelength of the inspection system.

10. An optical inspection system as recited in claim 4 wherein the broadband and the narrowband light sources produce light within the wavelength range of 100–600 nanometers.

11. An optical inspection system as recited in claim 4 wherein the broadband illumination source is a mercury or mercury-xenon lamp.

12. An optical inspection system as recited in claim 4 wherein the narrowband illumination source is a laser.

13. An optical inspection system as recited in claim 12, wherein the laser produces light at approximately 266 nanometers.

14. An optical inspection system as recited in claim 4 wherein the narrowband light beam is concentrated approximately equal to less than 300 nm.

15. An optical inspection system for semiconductor inspection comprising:
a broadband illumination source that directs a broadband light beam into the optical inspection system in order to illuminate a semiconductor specimen;
a first narrow band illumination source that directs a first narrowband light beam into the optical inspection system in order to farther illuminate the semiconductor specimen, wherein the broadband and the first narrowband light beams are coincident with each other at a first dichroic beamsplitter such that the broadband and the first narrowband light bears have approximately the name LaGrange Invariant, at the first dichroic beamsplitter; and
a second narrowband illumination source that directs a second narrowband light beam into the optical inspection system in order to further illuminate the semiconductor specimen, whereby the broadband, the first and second narrowband light beams are used together for inspection purposes.

16. An optical inspection system as recited in claim 15 wherein the second narrowband light beam becomes coincident with the broadband and the first narrowband light beams at a second dichroic beamsplitter such that the broadband, the first and the second narrowband light beams have approximately the same LaGrange Invariants at the second dichroic beamsplitter.

17. An optical inspection system as recited in claim 15 wherein the broadband light beam spans a first range of wavelengths wherein the intensity of light within the first range is lower at the lower end of the first rang; and wherein the first narrowband light beam spans a second range of wavelengths wherein the intensity of light within the second range is approximately constant, the second range of wavelengths being positioned within the lower end of the first range, and wherein the second narrowband light beam spans a third range of wavelengths wherein the intensity of light within the third range is approximately constant, the third range of wavelengths also being positioned within the lower end of the first range.

18. An optical inspection system as recited in claim 15 wherein the broadband light beam spans a first range of wavelengths wherein the intensity of light within the first range is lower at the lower end of the first range, and wherein the first narrowband light beam spans a second range of wavelengths wherein the intensity of light within the second range is approximately constant, the second range of wavelengths being positioned within the lower end of the first range, and wherein the second narrowband light beam spans a third range of wavelengths wherein the intensity of light within the third range is approximately constant, the third range of wavelengths being positioned within a higher end of the first range.

19. An optical inspection system for semiconductor inspection comprising:
a broadband illumination source that directs a broadband light beam into the optical inspection system in order to illuminate a semiconductor specimen; and
a narrow band illumination source that directs a narrowband light beam into the optical inspection system in order to further illuminate the semiconductor specimen, wherein the broadband light beam spans a first range of wavelengths, and wherein the narrowband light beam spans a second range of wavelengths, the second range of wavelengths being positioned within the shorter wavelength end of the first range thereby lowering the effective inspection wavelength of the inspection system, wherein the broadband and the narrow band illumination sources are coincident with each other at a dichroic beamsplitter such that the broadband and the narrow band illumination soirees have approximately the same LaGrange Invariants at the dichroic beamsplitter, whereby the broadband and the narrowband light beams are used together for inspection purposes.

20. An optical inspection system as recited in claim 19 wherein the broadband illumination source is a mercury or mercury-xenon lamp.

21. An optical inspection system as recited in claim 19 wherein the narrowband illumination source is a laser.

22. An illumination device as recited in claim 19 wherein the narrowband light beam is concentrated at approximately equal to or less than 300 nm.

* * * * *

UNITED STATES PATENT AND TRADEMARK OFFICE
CERTIFICATE OF CORRECTION

PATENT NO. : 6,788,404 B2
DATED : September 7, 2004
INVENTOR(S) : Steven R. Lange It is certified that error appears in the above-identified patent and that said Letters Patent is hereby corrected as shown below:

Column 8,
Line 58, change "the fist" to -- the first --.

Column 9,
Line 17, change "narrowband the broadband" to -- narrowband or the broadband --.
Line 49, change "concentrated approximately" to -- concentrated at approximately --
Line 50, change "equal to less than" to -- equal to or less than --.
Line 58, change "farther illuminate" to -- further illuminate --.
Line 62, change "light bears" to -- light beams --.
Line 63, change "name LaGrange Invariant" to -- same La Grange Invariants --.

Column 10,
Line 13, change "first rang;" to -- first range, --.
Line 53, change "soirees have" to -- sources have --.

Signed and Sealed this

Eighth Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,788,404 B2
DATED : September 7, 2004
INVENTOR(S) : Steven R. Lange It is certified that error appears in the above-identified patent and that said Letters Patent is hereby corrected as shown below:

Column 1,
Line 11, add the following new paragraph:
-- The U.S. Government has a paid-up license in this invention and the right in limited circumstances to require the patent owner to license others on reasonable terms as provided for by the terms of Cooperative Agreement Number 70NANB0H3038 awarded by NIST ATP. --

Signed and Sealed this

Seventeenth Day of May, 2005

JON W. DUDAS
*Director of the United States Patent and Trademark Office*